United States Patent [19]

Parks

[11] Patent Number: 5,401,890

[45] Date of Patent: Mar. 28, 1995

[54] PROCESS AND APPARATUS FOR HEAT TREATING HALOGENATED COMPOUNDS

[75] Inventor: John C. Parks, Baton Rouge, La.

[73] Assignee: Albemarle Corporation, Richmond, Va.

[21] Appl. No.: 907,587

[22] Filed: Jul. 2, 1992

Related U.S. Application Data

[60] Continuation-in-part of Ser. No. 844,202, Mar. 2, 1992, Pat. No. 5,302,768, which is a division of Ser. No. 559,655, Jul. 30, 1990, abandoned.

[51] Int. Cl.⁶ .................... C07C 17/38; C07C 22/00
[52] U.S. Cl. .................. 570/211; 570/184; 570/185
[58] Field of Search .................. 570/185, 184, 211

[56] References Cited

U.S. PATENT DOCUMENTS

| | | | |
|---|---|---|---|
| 2,033,612 | 3/1936 | Clark et al. | 260/161 |
| 2,244,284 | 6/1941 | Britton et al. | 260/649 |
| 3,141,860 | 7/1964 | Sauer et al. | 260/33.8 |
| 3,232,959 | 2/1966 | Hahn | 260/389 |
| 3,285,965 | 11/1966 | Jenkner | 260/612 |
| 3,331,797 | 7/1967 | Kopetz et al. | 260/28.5 |
| 3,763,248 | 10/1973 | Mitchell | 260/649 D |
| 3,833,674 | 9/1974 | Brackenridge | 260/649 DP |
| 3,959,387 | 5/1976 | Brackenridge | 260/612 R |
| 3,965,197 | 6/1976 | Stepniczka | 260/623 H |
| 4,287,373 | 9/1981 | Garman et al. | 568/639 |
| 4,327,227 | 4/1982 | Ayres et al. | 568/639 |
| 4,521,633 | 6/1985 | Pedjac | 568/639 |
| 4,569,596 | 2/1986 | Romanchik et al. | 366/107 |
| 4,639,481 | 1/1987 | Giles, Jr. | 524/128 |
| 4,659,021 | 4/1987 | Bark et al. | 241/18 |
| 4,666,947 | 5/1987 | Brichta et al. | 521/79 |
| 4,740,629 | 4/1988 | Brackenridge et al. | 568/639 |
| 4,830,773 | 5/1989 | Olson | 252/174.13 |
| 4,863,626 | 9/1989 | Coyne et al. | 252/91 |
| 5,200,236 | 4/1993 | Lang et al. | 427/213 |

FOREIGN PATENT DOCUMENTS

| | | |
|---|---|---|
| 708209 | 4/1965 | Canada . |
| 0265150 | 4/1988 | European Pat. Off. . |
| 2950877 | 6/1981 | Germany . |
| 39639 | 3/1977 | Japan . |
| 116332 | 10/1978 | Japan . |
| 116333 | 10/1978 | Japan . |
| 116334 | 10/1978 | Japan . |
| 70060 | 6/1981 | Japan . |
| 981833 | 1/1965 | United Kingdom . |
| 991067 | 5/1965 | United Kingdom . |
| 1411524 | 10/1975 | United Kingdom . |
| 1472383 | 5/1977 | United Kingdom . |

OTHER PUBLICATIONS

By Green et al. in 'Flame Retardants: Proceedings of 1974 International Symposium on Flammability and Fire Retardants', pp. 68–76, 1974

By Inaba et al. in the 'Journal of Organic Chemistry', 49 (12), pp. 2093–2098, 1984.

By Corey et al. in the 'Journal of Organicmetallic Chemistry', 210 (2), pp. 149–161, 1981.

By Gassman et al. in the 'Journal of Organic Chemistry', 47 (20), pp. 4002–4004, 1982.

CAS Registry Handbook—Reg. No. 84852-53-9.

"Flammfestmachen von Kunststoffen" by Dr. Hans Vogel, p. 49.

Primary Examiner—Robert L. Stoll
Assistant Examiner—Joseph D. Anthony
Attorney, Agent, or Firm—David E. LaRose; Edgar E. Spielman, Jr.

[57] ABSTRACT

This invention relates to an improved process and apparatus for preparing a product predominant in decabromodiphenylethane, the process comprising heat treating the product in a product treating and storage system for a period of time and at a temperature which are sufficient to reduce the amount of unreacted bromine in the product wherein the product treating and storage system comprises an insulated storage vessel, and a heated stream of carrier gas for carrying and suspending the product particles in the storage vessel during the heat treatment step.

1 Claim, 1 Drawing Sheet

PROCESS AND APPARATUS FOR HEAT TREATING HALOGENATED COMPOUNDS

This application is a continuation-in-part of application Ser. No. 844,202, filed Mar. 2, 1992, now U.S. Pat. No. 5,302,761, which is a division of application Ser. No. 559,655, filed Jul. 30, 1990, now abandoned.

BACKGROUND

This invention relates to an improvement in a process for preparing a product predominant in decabromodiphenylalkane. More particularly, this invention relates to a method and apparatus for heat-treating a product predominant in decabromodiphenylethane in order to reduce the amount of unreacted bromine in the product.

Polyhalogenated diphenylalkanes, e.g. decabromodiphenylethane, are known flame retardants for use in polyolefin and polystyrenic-based formulations. On a commercial basis, the polyhalogenated diphenylalkane is supplied to the formulation as a product predominant in the polyhalogenated diphenylalkane selected. The product would have a form and an impurity content which would be characteristic of the process used to produce it. If the product's physical characteristics, e.g. thermal stability, limit the formulation's processability, then the processor's desire for the product is limited at best. If the product's color is not white or at least near white, the product will be suitable for use in some formulations, however, the product's use may not be acceptable in formulations calling for a white or light color.

When preparing a polybrominated diphenylalkane predominant product such as decabromodiphenylethane, there is a tendency for the product to retain a substantial amount of unreacted bromine even after separation of the product from the reaction mass and drying. By "substantial amount" is meant more than about 1000 ppm bromine. Such a high content of unreacted bromine leads to a product having a color characteristic which is less desirable than products having much lower bromine contents. Until now, conventional drying and grinding techniques, such as disclosed by Ayres et al., U.S. Pat. No. 4,327,227 and Bark et al., U.S. Pat. No. 4,659,021 have been less successful in reducing a substantial amount of unreacted bromine in the isolated product.

SUMMARY OF THE INVENTION

This invention provides an improvement in a process for heat-treating a product predominant in decabromodiphenylethane whereby the amount of unreacted bromine in the product is substantially reduced. The process comprises heat treating the product in a product treating and storage system for a period of time and at a temperature which are sufficient to reduce the amount of unreacted bromine in the product. The product treating and storage system comprises an insulated storage vessel, and a heated stream of carrier gas for carrying and suspending the product particles in the storage vessel during the heat treatment step.

In another embodiment, this invention provides an apparatus for reducing the amount of unreacted bromine in a product predominant in decabromodiphenylethane. The apparatus comprises (a) a carrier gas stream sufficient to suspend at least a portion of the product particles for a period of time; (b) a means for heating the carrier gas stream to a temperature above about 180° C.; and (c) a storage vessel for suspending the product particles in the heated carrier gas stream during heat treating, the storage vessel having a carrier gas inlet and an exhaust gas outlet.

THE DRAWINGS

FIG. 1 is an illustration, not to scale of the apparatus for heat treating and storing a product predominant in decabromo-diphenylethane.

DETAILED DESCRIPTION

Figure 1:
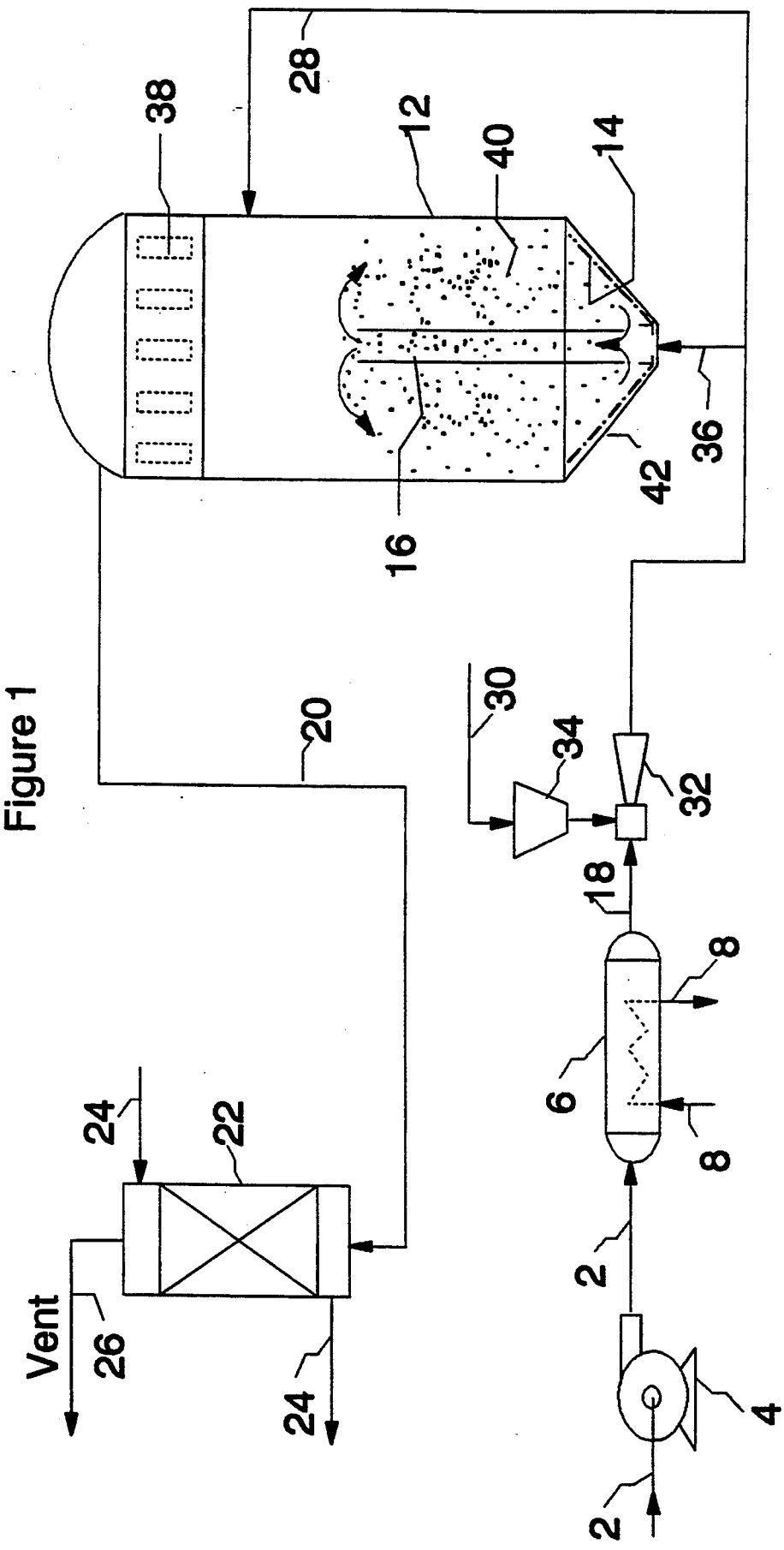

Accordingly, this invention provides an improvement in a process for preparing a product predominant in decabromodiphenylethane which is made by brominating diphenylethane in a reaction mass containing bromine and a bromination catalyst. The decabromodiphenylethane predominant product recovered from the reaction mass after brominating is first dried so as to form a solid particulate product predominant in decabromodiphenylethane and containing unreacted bromine. In order to reduce the amount of unreacted bromine in the product, the product is then heat treated in a product treating and storage system for a period of time and at a temperature which are sufficient to reduce the amount of unreacted bromine in the product. The product treating and storage system comprises an insulated and/or heat traced storage vessel, and a heated stream of carrier gas for carrying and suspending the product particles in the treating and storage vessel during the heat treatment step.

This invention also provides an apparatus for heat treating product particles predominant in decabromodiphenylethane.

The apparatus comprises (a) a carrier gas stream sufficient to suspend at least a portion of the product particles for a period of time; (b) a means for heating the carrier gas stream to a temperature above about $180\frac{1}{2}°$ C.; and (c) a storage vessel for suspending the product particles in the heated carrier gas stream during heat treating, the storage vessel having a carrier gas inlet and an exhaust gas outlet.

In order to better understand the invention, reference is now made to FIG. 1 which illustrates one embodiment of this invention. Prior to heat treating the product particles, the storage vessel 12 is charged with the solids 30 to be heat treated. To charge the storage vessel 12, carrier gas 2 is fed by blower 4 through heat exchanger 6 in order to heat the carrier gas to a temperature in the range of from about room temperature to about 100° C. The heating medium 8 for heating the carrier gas is heat transfer oil, steam, or hot air from a direct fired boiler. Preferably a heat transfer oil such as DOWTHERM-G heat transfer fluid is used to heat the carrier gas. Product particles 30 to be treated are fed from feed hopper 34 into heated carrier gas be via solids eductor 32. The carrier gas initially containing product particles is transferred through conduit 28 into the treating and storage vessel 12. Once the treating and storage vessel is fully charged, the temperature of the carrier gas 18 is increased to a range of from about 180° to about 235° C. for the heat treating process. During the heat treating step, a substantial portion of product particles 40 to be heat treated, e.g. greater than about 80 wt. %, have been initially charged to the treating and storage vessel 12 hence the use of feed hopper 34 and solids eductor 32 is greatly reduced. Heat is applied to product particles 40 in the treating and storage vessel through conduit 36, internal eductor 16 and carrier gas foraminous distributor 14 which is within the lower conical head of the silo 42. Internal eductor 16 serves to pick up and circulate product particles 40 from the lower portion of treating and storage vessel 12 to the upper portion of the vessel during the heat treating step while distributor 14 provides even distribution of the carrier gas for fluidizing the product particles. During the heat treating step, a substantial portion of product particles 40 in vessel 12 are suspended or fluidized by distributor 14 and internal eductor 16. By "substantial portion" is meant more than about 50 wt. % of the product particles in the vessel. During the product charging and heat treating steps the carrier gas is exhausted from vessel 12 through solids separator 38 which is located in the upper portion of the vessel. The essentially particle free carrier gas 20 may contain halogen and/or halogen halide during the heat treating step, hence, the carrier gas 20 is preferably fed to neutralizer 22 wherein it is contacted with neutralizing medium 24. Essentially halogen free carrier gas 26 may then be vented or further treated before venting to the atmosphere.

In order to reduce the amount of bromine in the product particles, it is a key feature of this invention, that the product particles be heated to a temperature and for a period of time which are sufficient to substantially reduce the amount of unreacted bromine in the product particles. The temperature is preferably greater than about 150° C., more preferably from about 180° to about 350° C. and most preferably from about 185° to about 250° C. Higher temperatures may be used to reduce the heat treating time proved the temperature is maintained below the melting or decomposition point of the particles to be heat treated.

It is preferred that the heat treating be conducted for a period of time greater than about 30 minutes preferably greater than about 45 minutes and most preferably from about 1 hour to about 20 hours. Normally a product having less than about 1000 ppm bromine can be obtained in 4 to 8 hours. However, the heat treating time will vary with the scale of equipment used, and the amount of product to be heat treated.

Without desiring to be bound by theory, it is believed that the bromine in the decabromodiphenylethane molecule is retained in the molecule in the form of a complex with the ar-brominated diphenylethane. Due to this complex, it has been found that drying and grinding procedures generally applicable to ar-brominated diphenyloxide products for removal of entrained bromine, are less successful when applied to decabromodiphenylethane for removal of entrained bromine. Instead of removal of the entrained bromine in the decabromodiphenylethane molecule, at least a portion of the bromine during the heat treating step reacts with the alkylene bridge to form a minor amount of 1,2-dibromo-bis-pentabromophenylethane.

While the foregoing heat treatment process is particularly useful in heat treating decabromodiphenylethane predominant products, it may also be used in preparing other decabromodiphenylalkane products made be brominating diphenylalkane. The diphenylalkane reactant used in preparing the decabromodiphenylalkane predominant product can be represented by the formula:

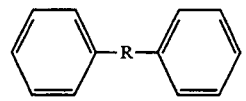

wherein R is an alkylene group containing 1 to 10 carbon atoms. Preferred R groups are methylene and ethylene which give, respectively, the preferred reactants, diphenylmethane and 1,2-diphenylethane. Exemplary of other diphenylalkanes are: 1-methyl-1,2-diphenylethane, 1,4-diphenylbutane, 1,6-diphenylhexane, 2,3-dimethyl-1,4-diphenylbutane, 2-ethyl-3-methyl-1,4-diphenylbutane, 2-methyl-1,7-diphenylhexane, 1,9-diphenylnonane and 1,10-diphenyldecane. The diphenylalkane reactant can be produced by various routes. For example, CA 97 38651d (Japanese Kokai 82/45114) and CA 46 7084 g disclose the reaction of benzene and ethylene dihalide in the presence of aluminum trichloride to yield diphenylalkane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities. These impurities often contribute to giving the final decabromodiphenylalkane product an off color. Exemplary of these color-causing impurities are benzene, toluene, ethylbenzene, diphenylmethane, the methyl and ethyl derivatives of 1,2-diphenylethane, and the like. Diminishing the impurity content can be accomplished in a conventional manner, for example, the diphenylalkane can be recrystallized.

In the preparation of decabromodiphenylalkane, e.g. decabromodiphenylethane, diphenylalkane is fed to the reaction vessel in a molten state. Thus, the diphenylalkane is at a temperature above its melting point but not so high that it experiences degradation. For diphenylethane, the melting point is about 53° C. to 55° C. and, hence, the diphenylethane is preferably fed at a temperature of from about 55° to about 80° C. The higher temperatures are preferred as the viscosity of the molten diphenylethane can be lower thus making its feed to the reaction vessel more convenient. Most preferred is a temperature within the range of from about 70° C. to about 80° C.

It is most desirable to provide a non-oxidizing atmosphere for the diphenylalkane until it is fed into the reaction vessel. Such an atmosphere can be provided by most inert gases. For example, nitrogen, argon, neon, helium, krypton, xenon, and the like. By providing the inert atmosphere, it has been found that the color characteristics of the product are benefitted.

It has also been found that the bromine utilized in the process of this invention should contain 10 ppm or less organic impurities, e.g. oil, grease, carbonyl containing hydrocarbons, iron and the like, so that there is little, if any, impact on the color attributes of the product. Commercial grade bromine having such purity may be available. If such is not available, the organic impurities and water content of the bromine can be conveniently reduced by mixing together a 3 to 1 volume ratio of bromine and concentrated (94–98 percent) sulfuric acid. A two phase mix is formed which is stirred for 10–16 hours. After stirring and settling, the sulfuric acid phase, along with the impurities and water, is separated from the bromine phase. To further enhance the purity of the bromine, the recovered bromine phase can be subjected to distillation.

The bromination catalyst used in the process of this invention is preferably $AlCl_3$ and/or $AlBr_3$, although use may be made of aluminum powder, iron powder, $FeCl_3$, and $FeBr_3$, alone or in combination with the aluminum trihalide(s). Other bromination catalysts are suitable, provided that they have sufficient catalytic activity to provide for the extent of bromination called for under the process conditions which will be encountered. Catalytic quantities are used. Typically, the catalysts will be present in an amount within the range of about 0.1 to about 20 weight percent, based on the weight of the diphenylalkane reactant used in the process. A preferred amount is within the range of from about 8 to about 15 weight percent on the same basis, with from about 9.0 to about 11.0 weight percent being most preferred.

The bromination catalyst and bromine can be charged to the reaction vessel in any order or together. It is preferred that both be cooled or heated, as the case may be, prior to their charging so that they will form a mix which is at least near the temperature at which the reaction mass will be maintained during the diphenylalkane addition. While the foregoing is a preferred technique, it is possible, though maybe not as convenient, for the catalyst and bromine, prior to charging, to be at temperatures other than the diphenylalkane addition temperature. If, prior to charging, the catalyst and bromine temperatures are above the addition temperature, the temperature of the resultant mix in the reaction vessel can be lowered to obtain the desired addition temperature. However, care should be taken not to aspirate atmospheric moisture into the reaction vessel during such lowering. The presence of moisture in the reaction vessel is detrimental as many bromination catalysts are deactivated by contact with water.

The amount of elemental bromine ($Br_2$) charged to the reaction vessel should provide sufficient bromine to effect the degree of bromination sought and to provide an easily stirred reaction mass. Generally, from about 15 to about 30 moles of bromine per mole of diphenylalkane feed will be suitable. Preferably from about 17 to about 25 moles of bromine per mole of diphenylalkane are used. A most preferred amount is in the range of from about 18 to about 23 moles of bromine per mole of phenylalkane. After the reaction is complete, the bromine not used in the ar-substitution will be a liquid component of the reaction mass and will continue to serve the before-mentioned purpose of providing a stirrable reaction mass.

The diphenylalkane addition generally occurs over a period of time and the addition rate is dependent upon the scale of the reaction and the ability to control the temperature and to handle hydrogen bromide evolution. On a commercial scale, the addition could involve about 1.0 to about 10.0 hours or longer.

During the diphenylalkane addition, the reaction mass temperature is kept below about 60° C., and preferably within the range of from 15° to 58° C. Since the bromination of diphenyl alkane is exothermic, cooling of the reaction mass during the diphenylalkane feed will be needed to obtain the addition temperature as required above. The heat of reaction can be removed from the reaction mass by cooling the reaction vessel or by having the reaction mass under reflux conditions so that heat can be removed by the use of an overhead condenser. The rate of diphenylalkane addition will be dependent upon the ability of the equipment to maintain the selected addition temperature.

It is preferred that the diphenylalkane be added to the reaction vessel containing bromine and a bromination catalyst. This addition can be performed either supersurface or subsurface to the liquid bromine in the reaction vessel. It is particularly preferred to add the diphenylalkane subsurface to the liquid bromine in the reaction vessel in order to form the largest size particles. It is also particularly preferred to charge the diphenylalkane at a linear velocity which achieves the greatest particle size. Such velocity is in the range of from about 0.25 to about 10 meters per second, preferably from about 0.5 to 5 meters per second.

The bromination reaction can be accomplished at a pressure ranging from subatmospheric to superatmospheric. While the selected pressure is not critical to the invention, from a standpoint of ease of operation, it is desirable to utilize a pressure slightly above atmospheric pressure. Preferably, the pressure is above about 19 psia and most preferably, the pressure is in a range of from about 20 to about 30 psia.

It has been found that the bromination reaction is quite rapid when the diphenylalkane to be brominated is 1,2-diphenylethane. Hence, after completion of the addition of diphenylethane reactant to the reaction mass, there is little need to maintain a ride time at a temperature near or above the reaction temperature to assure substantially complete ar-bromination of the diphenylethane reactant. It may however, be desirable to maintain a post feed ride time at an elevated temperature for the ar-bromination of other diphenylalkane reactants. When a post feed ride time is desired, the reaction mass is brought to a temperature within the range of from about 55° C. to reflux after the addition of the diphenylalkane reactant is complete.

After the post feed ride time, or in the case of diphenylethane, shortly after completion of the addition of diphenylethane, e.g. after about 2 or 3 minutes, the average bromine number of the ar-brominated diphenylalkane is generally at least about 9.0. The average bromine number is defined as the average number of bromine atoms ar-substituted on each brominated diphenylalkane molecule in the product. Thus, an average bromine number of 9.0 indicates that not all of the diphenylalkane molecules in the product have been ring perbrominated, hence, the presence of the lower bromo homologs, e.g. nonobromodiphenylalkane, octabromodiphenylalkane, etc., in the product. As the average bromine number approaches 10.0, the amount of these lower bromo homologs will decrease and the amount of the decabromohomolog will increase.

After substantial completion of the addition of the diphenylalkane reactant, the reaction mass will comprise a liquid-solid mixture. The solid comprises brominated diphenylalkane, catalyst, entrained bromine and other impurities. The liquid will comprise mostly bromine. The brominated diphenylalkane can be separated from the product by steam stripping to remove the non-entrained bromine from the reaction mass and to deactivate the catalyst. The remaining solids are then washed with an aqueous base, e.g. an aqueous solution of NaOH or $Na_2CO_3$, to neutralize and remove any HBr present. A final water washing step is used to obtain a product which is predominant, i.e. 50+weight percent, in decabromodiphenylalkane. This product is of good color and is further treated to have superior color. A preferred product is one which contains 85+weight percent, and most preferably 90+weight percent, decabromodiphenylalkane.

A key feature of this invention is the heat treating step which is performed subsequent to separation of the decabromodiphenylalkane product from the reaction mass. Heat treating the product provides a product with less than about 1000 ppm, preferably, less than 500 ppm, and most preferably, less than about 200 ppm free bromine in the product. This heat treatment step may be performed before or after the product is dried and/or the particle size of the product reduced if desired. During the heat treatment step, the product is maintained at a temperature and for a period of time which are sufficient to form the decabromodiphenylalkane predominant product containing a minor amount of dodecabromodiphenylalkane. By a minor amount is meant less than about 20 weight percent based the total amount of dried and treated product thus obtained. Preferably the amount of dodecabromodiphenylalkane is in a range of from about 0.1 weight percent to about 10 weight percent and most preferably in the range of from about 0.4 weight percent to about 8 weight percent. The before mentioned apparatus and heat treating process are particularly useful in performing the heat treating operation.

The decabromodiphenylalkane product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber, and polysiloxanes. The polymer may also be a blend of various polymers. Further, the polymer may be, where appropriate, cross-linked by chemical means or by irradiation.

The amount of product used in a formulation will be that quantity needed to obtain the flame retardancy sought. It will be apparent to those skilled in the art that for all cases no single precise value for the proportion of the product in the formulation can be given, since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 weight percent, preferably 10 to 30 percent, of the product when it is the only flame retardant compound in the formulation.

It is especially advantageous to use the product with an inorganic compound, especially ferric oxide, zinc oxide, zinc borate, the oxide of a Group V element, for example, bismuth, arsenic, phosphorus and especially antimony, in the formulation. Of these compounds, antimony oxides is especially preferred. If such a compound is present in the formulation, the quantity of product needed to achieve a given flame-retardancy is accordingly reduced. Generally, the product and the inorganic compound are in a weight ratio of from about 1:1 to about 7:1; and preferably of from about 2:1 to about 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g. plasticizers, antioxidants, fillers, pigments, UV stabilizers, etc. can be used in formulation with the product of this invention.

Thermoplastic articles formed from formulations containing a thermoplastic polymer and a product of this invention can be produced conventionally, e.g. by injection molding, extrusion molding, compression molding, and the like.

The following Examples merely illustrate the invention described herein and are not to be taken as limiting such inventions.

EXAMPLE 1

Preparation of Decabromodiphenylethane

A 19,000 liter glass-lined reactor was equipped with a mechanical stirrer, a reflux condenser, a temperature sensor, a dip pipe addition line, and a caustic scrubber. The reactor was charged with bromine (15,124 kilograms, 208.4 moles) and anhydrous aluminum chloride (79 kilograms, 1.31 moles). The reactor was then heated to about 54° C. and molten diphenylethane (DPE) (743 kilograms, 8.98 moles, 99.3 weight percent DPE) was added through a dip-tube to the reactor contents. The addition of DPE took about 4 hours. During the addition, the pressure in the reaction vessel was maintained at about 20 psia (138 KPa) and the reactor was cooled so as to maintain a temperature of about 56° C. A sample taken 14 minutes after completion of the DPE feed was 98.99 weight percent decabromodiphenylethane by gas chromatography analysis (GC) for a 91.5 percent overall yield.

After the DPE feed was complete, the reactor contents were transferred to a stripper vessel containing 3406 liters of water. The stripper vessel contents were then heated with steam until the temperature was about 98° C. and the excess bromine was distilled from the product and condensed. Free water was allowed to drain back to the stripper vessel resulting in aqueous slurry of decabromodiphenylethane predominant product and water. After bromine removal, stripper,vessel contents were cooled and 814 liters of 25 percent caustic (2.01 percent excess) were added. The stripper vessel contents were pumped to a slurry tank and from the slurry tank, pumped batchwise to the centrifuge where the solid decabromodiphenylethane predominant product was recovered as a wet cake. The wet cake was washed with fresh water until the centrate was at a pH of about 8.0 and the wet cake was then ground and dried in a Raymond mill dryer/grinder. Analysis of the dried product indicated about 6000 ppm free bromine, a melting point range of about 346° to 359° C., and Hunter color values of L=83.2–84.2, a=2.51–3.03 and b=18.8–20.1, and a yellowness index (Y.I.)=42.0–45.6.

EXAMPLE 2

(Comparative Example)

Decabromodiphenylethane predominant product made generally in accordance with the procedure of Example 1 was dried then heat treated in a double-cone, tumble dryer at 230° C. for 40 hours. The heat treated product had a melting point of 349° C. and Hunter color values of L=80.4, a=0.5, b=7.5 and Y.I.=17.2. GC analysis of the heat treated product indicated about 5.2 weight percent 1,2-dibromo-bis-pentabromophenylethane and 94.8 weight percent decabromodiphenylethane.

The following example illustrates the process and advantages of this invention.

EXAMPLE 3

Decabromodiphenylethane predominant product made generally in accordance with Example 1 had the following color characteristics, yellowness index (Y.I.) 37.04, Hunter L value 86.91, and Hunter b value 17.25. The product was divided into six 3178 kilogram portions and each portion was charged to a fluidized bed silo (1.25 meters in diameter and 4.75 meters high) for heat treatment. The silo was equipped with DOWTHERM-J heat tracing and reactor jacket in order to maintain the silo skin temperature at about 230° C. during the heat treatment. Air (930 scfm) heated to 235° C. using a DOWTHERM-G heater and finned tube heat exchanger was fed into the fluidized bed silo through a vertical internal induction tube (1.5 mm in diameter, 3 meters long). Within the bottom head of the silo was a inverted conical-shaped foraminous distributor plate which provided hot air distribution and fluidization of the product particles during heat treatment. The product particles were maintained at an average temperature of 230° C. for 6 hours during the heat treatment step. After heat treatment GC analysis of the heat treated product indicated that the product contained about 99.3 wt. % decabromodiphenylethane, and 0.7 wt. % 1,2-dibromo-bis-pentabromophenylethane. The color characteristics of the heat treated product prepared using the process and apparatus of this invention are given in Table 1.

TABLE 1

| Sample # | Yellowness Index (Y.I.) | Hunter L value | Hunter b value |
| --- | --- | --- | --- |
| 1 | 11.65 | 89.13 | 5.85 |
| 2 | 11.81 | 90.03 | 5.98 |
| 3 | 11.6 | 89.16 | 5.81 |
| 4 | 11.72 | 90.26 | 5.96 |
| 5 | 12.27 | 90.88 | 6.27 |
| 6 | 12.09 | 90.11 | 6.12 |
| Composite | 11.98 | 90.17 | 6.07 |

Variations of the process of this invention are within the spirit and scope of the appended claims.

What is claimed is:

1. A process for reducing the unreacted bromine content of unground dried decabromodiphenylethane particles, which particles were produced by the perbromination of diphenylethane and which dried particles initially contain at least 1000 ppm unreacted bromine, the process consisting essentially of, suspending and heating the dried unground particles with a hot carrier gas, the hot carrier gas heating the dried unground particles to a temperature within the range of from about 180° to about 350° C. for a period sufficient to obtain a bromine content for the heated particles of less than about 200 ppm unreacted bromine.

* * * * *